US012336861B2

(12) United States Patent
Sakamoto et al.

(10) Patent No.: US 12,336,861 B2
(45) Date of Patent: Jun. 24, 2025

(54) DIAGNOSTIC ASSISTANCE DEVICE, DIAGNOSTIC ASSISTANCE SYSTEM, AND DIAGNOSTIC ASSISTANCE METHOD

(71) Applicants: TERUMO KABUSHIKI KAISHA, Tokyo (JP); Rokken Inc., Sakai (JP)

(72) Inventors: Yasukazu Sakamoto, Hiratsuka (JP); Katsuhiko Shimizu, Fujinomiya (JP); Hiroyuki Ishihara, Tokyo (JP); Clément Jacquet, Sakai (JP); Thomas Henn, Sakai (JP); Nuwan Herath, Nancy (FR); Iselin Erikssen, Osaka (JP); Ryosuke Saga, Osaka (JP)

(73) Assignees: TERUMO KABUSHIKI KAISHA, Tokyo (JP); ROKKEN INC., Sakai (JP)

( * ) Notice: Subject to any disclaimer, the term of this patent is extended or adjusted under 35 U.S.C. 154(b) by 424 days.

(21) Appl. No.: 17/708,227

(22) Filed: Mar. 30, 2022

(65) Prior Publication Data
US 2022/0218311 A1 Jul. 14, 2022

Related U.S. Application Data

(63) Continuation of application No. PCT/JP2020/036433, filed on Sep. 25, 2020.

(30) Foreign Application Priority Data

Sep. 30, 2019 (JP) ................. 2019-178979

(51) Int. Cl.
*A61B 8/00* (2006.01)
*A61B 8/13* (2006.01)
(Continued)

(52) U.S. Cl.
CPC .............. *A61B 8/5207* (2013.01); *A61B 8/13* (2013.01); *A61B 8/466* (2013.01); *A61B 8/483* (2013.01);
(Continued)

(58) Field of Classification Search
CPC ......... A61B 8/5207; A61B 8/13; A61B 8/466; A61B 8/483; A61B 8/54; A61B 5/6852;
(Continued)

(56) References Cited

U.S. PATENT DOCUMENTS 6,251,072 B1   6/2001   Ladak et al.
6,385,332 B1   5/2002   Zahalka et al.
(Continued)

FOREIGN PATENT DOCUMENTS

CN   111127572   *   5/2020   .............. G06T 7/90
JP       2756047   *   5/1998
(Continued)

*Primary Examiner* — Jerome Grant, II
(74) *Attorney, Agent, or Firm* — Buchanan Ingersoll & Rooney PC

(57) ABSTRACT

A diagnostic assistance device is a diagnostic assistance device configured to generate three-dimensional data of a biological tissue based on tomographic data of the biological tissue, and display the generated three-dimensional data as a three-dimensional image on a display. The diagnostic assistance device includes a control unit configured to adjust a color tone of each voxel of the three-dimensional image according to a distance from a reference point, a reference line, or a reference plane in a three-dimensional space to each point of the three-dimensional data.

7 Claims, 12 Drawing Sheets

(51) Int. Cl.
*G06T 7/60* (2017.01)
*G06T 15/08* (2011.01)
*G06T 19/20* (2011.01)

(52) U.S. Cl.
CPC ............... *A61B 8/54* (2013.01); *G06T 7/60* (2013.01); *G06T 15/08* (2013.01); *G06T 19/20* (2013.01); *G06T 2207/10072* (2013.01); *G06T 2207/30004* (2013.01); *G06T 2219/2012* (2013.01)

(58) Field of Classification Search
CPC ... A61B 5/7475; A61B 5/0073; A61B 5/0084; A61B 5/742; A61B 8/0891; A61B 5/0066; A61B 8/12; G06T 7/60; G06T 15/08; G06T 19/20; G06T 2207/10072; G06T 2207/30004; G06T 2219/2012
USPC ........................................................ 382/131
See application file for complete search history.

(56) References Cited

U.S. PATENT DOCUMENTS

| | | | | |
|---|---|---|---|---|
| 7,623,704 | B2* | 11/2009 | Sasaki | H04N 1/62 345/589 |
| 11,593,989 | B1* | 2/2023 | Krol | H04L 12/1827 |
| 2002/0036824 | A1* | 3/2002 | Sasaki | G02B 21/16 359/368 |
| 2002/0055133 | A1* | 5/2002 | Hahn | C07K 1/1077 548/452 |
| 2010/0215238 | A1 | 8/2010 | Lu et al. | |

FOREIGN PATENT DOCUMENTS

| | | | | |
|---|---|---|---|---|
| JP | 2001255864 | * | 9/2001 | |
| JP | 2012005593 A | | 1/2012 | |
| JP | 2012005593 | * | 6/2014 | |
| JP | 2017092514 | * | 5/2017 | |
| WO | W)2020163567 | * | 8/2020 | ............ G01B 11/06 |

* cited by examiner

DIAGNOSTIC ASSISTANCE DEVICE, DIAGNOSTIC ASSISTANCE SYSTEM, AND DIAGNOSTIC ASSISTANCE METHOD

CROSS-REFERENCES TO RELATED APPLICATIONS

This application is a continuation of International Application No. PCT/JP2020/036433 filed on Sep. 25, 2020, which claims priority to Japanese Application No. 2019-178979 filed on Sep. 30, 2019, the entire content of both of which is incorporated herein by reference.

TECHNOLOGICAL FIELD

The present disclosure generally relates to a diagnostic assistance device, a diagnostic assistance system, and a diagnostic assistance method.

BACKGROUND DISCUSSION

U.S. Patent Application Publication No. 2010/0215238, U.S. Pat. Nos. 6,385,332, and 6,251,072 disclose a technique of generating a three-dimensional image of a cardiac cavity or a blood vessel using an ultrasound (US) image system.

Treatment using intravascular ultrasound (IVUS) is widely performed on a cardiac cavity, a cardiac blood vessel, a lower limb artery region, and the like. The IVUS is a device or a method for providing a two-dimensional image of a plane perpendicular to a long axis (longitudinal axis) of a catheter.

At present, an operator needs to perform treatment while reconstructing a three-dimensional structure by stacking two-dimensional images of IVUS in his/her brain, which can be a barrier particularly to young doctors or inexperienced doctors. In order to remove such a barrier, it is conceivable to automatically generate a three-dimensional image representing a structure of a biological tissue such as a cardiac cavity or a blood vessel from the two-dimensional images of IVUS and display the generated three-dimensional image toward the operator. When the three-dimensional image is to be displayed, it is conceivable to add shading to the three-dimensional image to express unevenness and depth in a three-dimensional space.

However, when the color tone is the same, it is difficult for the operator to grasp the unevenness and depth.

SUMMARY

The present disclosure facilitates grasping of unevenness or depth in the three-dimensional space for the operator of a diagnostic assistance device.

A diagnostic assistance device according to an aspect of the present disclosure is a diagnostic assistance device configured to generate three-dimensional data of a biological tissue based on tomographic data of the biological tissue, and display the generated three-dimensional data as a three-dimensional image on a display. The diagnostic assistance device includes a control unit configured to adjust a color tone of each voxel of the three-dimensional image according to a distance from a reference point, a reference line, or a reference plane in a three-dimensional space to each point of the three-dimensional data.

In one embodiment, the control unit is configured to form, in the three-dimensional data, an opening that exposes an inner wall surface of the biological tissue to an outside of the biological tissue in the three-dimensional image, and adjust a position of the reference point, the reference line, or the reference plane according to a position of the formed opening.

In one embodiment, the control unit is configured to arrange the reference point on a straight line in a cross section of the biological tissue that passes through a viewpoint when the three-dimensional image is displayed on the display and a midpoint of a straight line connecting a first end edge of the opening and a second end edge of the opening.

In one embodiment, the control unit is configured to arrange the reference point on a straight line drawn perpendicularly to a straight line connecting a first end edge of the opening and a second end edge of the opening from a midpoint of the straight line.

In one embodiment, when at least a part of a point group in the three-dimensional data in a range to be displayed on the display as the three-dimensional image has a difference in color tone with respect to a difference in distance from the reference point, the reference line, or the reference plane that does not satisfy a condition, the control unit corrects the color tone of each voxel of the three-dimensional image in accordance with the condition.

In one embodiment, the diagnostic assistance device further includes an input unit configured to receive an operation of a user. The control unit is configured to receive, via the input unit, an operation of changing a difference in color tone with respect to a difference in distance from the reference point, the reference line, or the reference plane of at least a part of a point group in the three-dimensional data in a range to be displayed on the display as the three-dimensional image, and change the color tone of each voxel of the three-dimensional image in response to the received operation.

In one embodiment, the diagnostic assistance device further includes an input unit configured to receive an operation of a user. The control unit is configured to receive, via the input unit, an operation of changing a position of the reference point, the reference line, or the reference plane, and change the color tone of each voxel of the three-dimensional image in response to the received operation.

A diagnostic assistance system according to an aspect of the present disclosure includes the diagnostic assistance device and a sensor configured to acquire the tomographic data while moving in the biological tissue.

In one embodiment, the diagnostic assistance system further includes the display.

A diagnostic assistance method according to an aspect of the present disclosure is a diagnostic assistance method for generating three-dimensional data of a biological tissue based on tomographic data of the biological tissue, and displaying the generated three-dimensional data as a three-dimensional image on a display. The diagnostic assistance method includes adjusting a color tone of each voxel of the three-dimensional image according to a distance from a reference point, a reference line, or a reference plane in a three-dimensional space to each point of the three-dimensional data.

According to the present disclosure, it is easy for a user to grasp unevenness or depth in a three-dimensional space.

DETAILED DESCRIPTION

Figure 1:
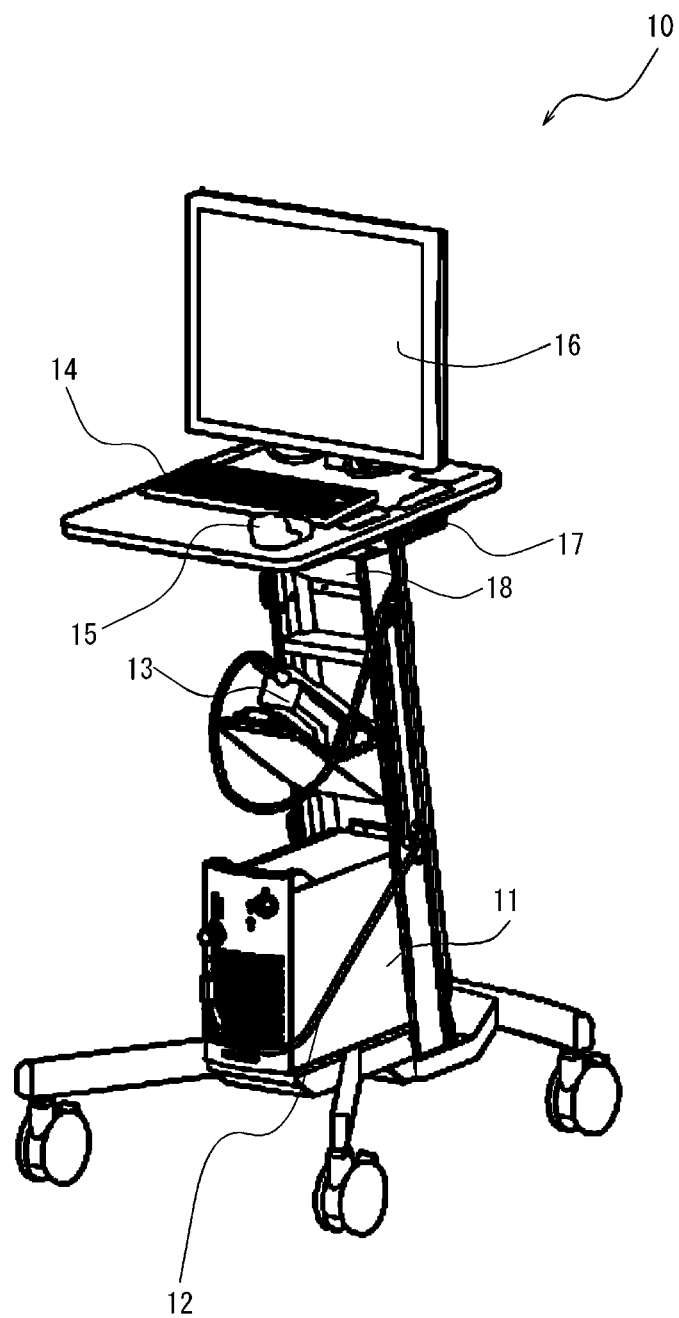
FIG. 1 is a perspective view of a diagnostic assistance system according to an embodiment.

Set forth below with reference to the accompanying drawings is a detailed description of embodiments of a diagnostic assistance device, a diagnostic assistance system, and a diagnostic assistance method representing examples of the inventive diagnostic assistance device, diagnostic assistance system, and diagnostic assistance method.

In the drawings, the same or corresponding parts are denoted by the same reference numerals. In the description of the present embodiment, the description of the same or corresponding parts will be omitted or simplified as appropriate.

Figure 3:
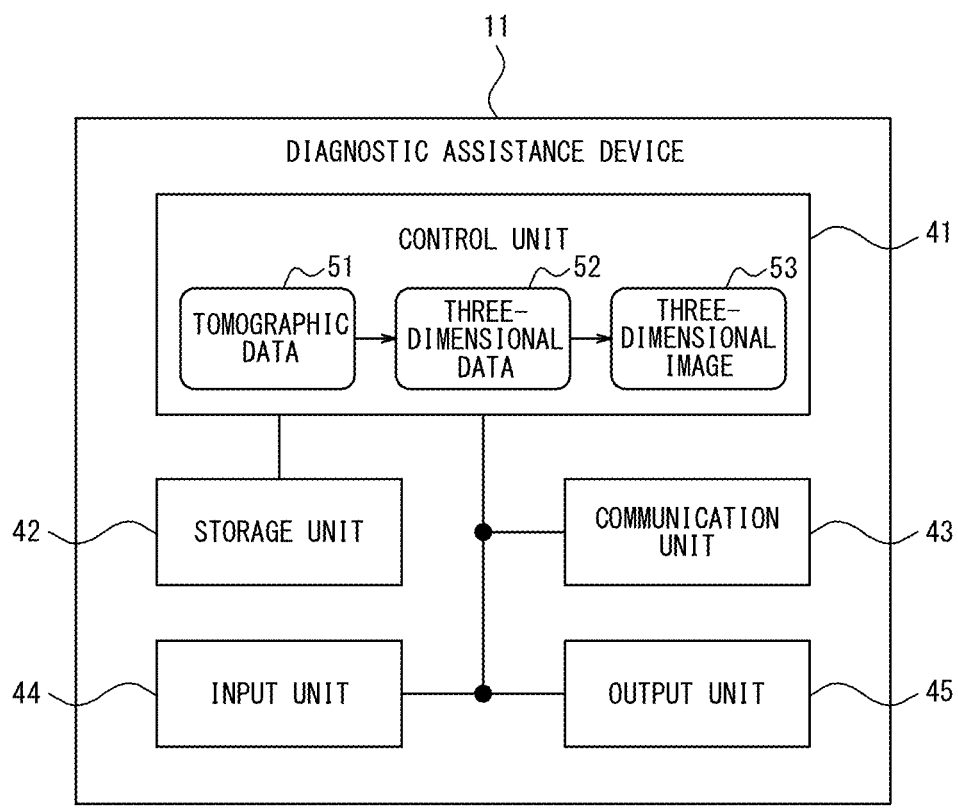
FIG. 3 is a block diagram showing a configuration of a diagnostic assistance device according to the embodiment.

An outline of the present embodiment will be described with reference to FIGS. 1, 3, and 5.

A diagnostic assistance device 11 according to the present embodiment generates three-dimensional data 52 of a biological tissue 60 based on tomographic data 51 of the biological tissue 60. The diagnostic assistance device 11 displays the generated three-dimensional data 52 as a three-dimensional image 53 on a display 16. The diagnostic assistance device 11 adjusts a color tone of each voxel of the three-dimensional image 53 according to a distance from a reference point Ps in a three-dimensional space to each point of the three-dimensional data 52.

According to the present embodiment, it is relatively easy for a user to grasp unevenness or depth in the three-dimensional space. For example, when the user is an operator, it can be relatively easy to grasp a shape of the biological tissue 60, which facilitates treatment.

The biological tissue 60 can be, for example, an organ such as a blood vessel or a heart.

A configuration of a diagnostic assistance system 10 according to the present embodiment will be described with reference to FIG. 1.

The diagnostic assistance system 10 includes the diagnostic assistance device 11, a cable 12, a drive unit 13, a keyboard 14, a mouse 15, and the display 16.

The diagnostic assistance device 11 can be a dedicated computer specialized for image diagnosing in the present embodiment, but may also be a general-purpose computer such as a personal computer (PC).

The cable 12 is used to connect the diagnostic assistance device 11 and the drive unit 13.

Figure 2:
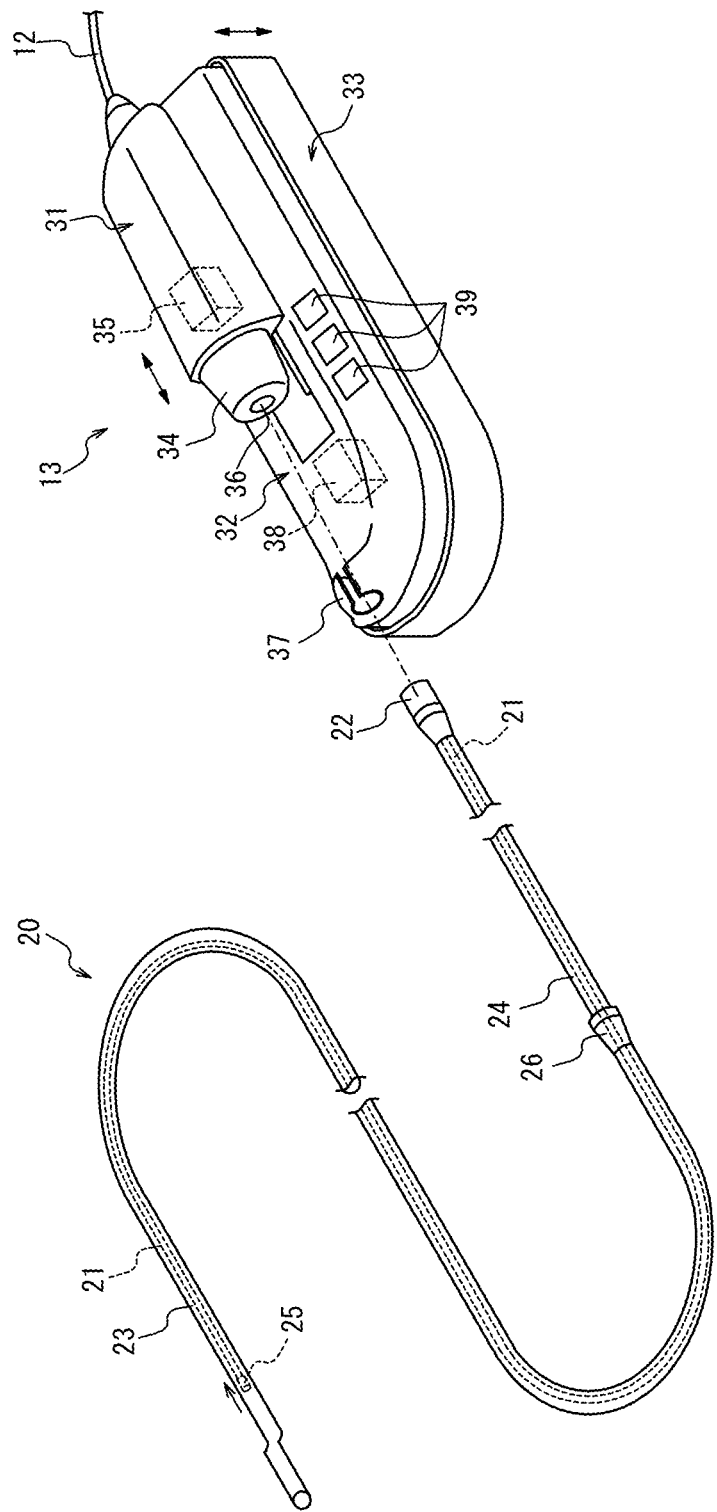
FIG. 2 is a perspective view of a probe and a drive unit according to the embodiment.

The drive unit 13 is a device to be used by connecting to a probe 20 shown in FIG. 2 to drive the probe 20. The drive unit 13 is also referred to as a motor drive unit (MDU). The probe 20 can be applied to IVUS. The probe 20 is also referred to as an IVUS catheter or an image diagnostic catheter.

The keyboard 14, the mouse 15, and the display 16 are connected to the diagnostic assistance device 11 via any cable or wirelessly. The display 16 can be, for example, a liquid crystal display (LCD), an organic electro luminescence (EL) display, or a head-mounted display (HMD).

The diagnostic assistance system 10 optionally further includes a connecting terminal 17 and a cart unit 18.

The connecting terminal 17 is used to connect the diagnostic assistance device 11 and an external device. The connecting terminal 17 can be, for example, a universal serial bus (USB) terminal. The external device can be, for example, a recording medium such as a magnetic disc drive, a magneto-optical disc drive, or an optical disc drive.

The cart unit 18 can be a cart equipped with casters for movement. The diagnostic assistance device 11, the cable 12, and the drive unit 13 are disposed on a cart body of the cart unit 18. The keyboard 14, the mouse 15, and the display 16 are disposed on an uppermost table of the cart unit 18.

A configuration of the probe 20 and the drive unit 13 according to the present embodiment will be described with reference to FIG. 2.

The probe 20 includes a drive shaft 21, a hub 22, a sheath 23, an outer tube 24, an ultrasound transducer 25, and a relay connector 26.

The drive shaft 21 passes through the sheath 23 to be inserted into a body cavity of a living body and the outer tube 24 connected to a proximal end of the sheath 23, and extends to an inside of the hub 22 provided at a proximal end of the probe 20. The drive shaft 21 is provided with the ultrasound transducer 25, which transmits and receives signals, at a distal end of the drive shaft 21, and is rotatably provided in the sheath 23 and the outer tube 24. The relay connector 26 connects the sheath 23 and the outer tube 24.

The hub 22, the drive shaft 21, and the ultrasound transducer 25 are connected to each other so as to integrally move forward and backward in an axial direction. Therefore, for example, when the hub 22 is pressed toward a distal side, the drive shaft 21 and the ultrasound transducer 25 move inside the sheath 23 toward the distal side. For example, when the hub 22 is pulled toward a proximal side, the drive shaft 21 and the ultrasound transducer 25 move inside the sheath 23 toward the proximal side as indicated by arrows.

The drive unit 13 includes a scanner unit 31, a slide unit 32, and a bottom cover 33.

The scanner unit 31 is connected to the diagnostic assistance device 11 via the cable 12. The scanner unit 31 includes a probe connection unit 34 connected to the probe 20, and a scanner motor 35 which is a drive source for rotating the drive shaft 21.

The probe connection unit 34 is detachably connected to the probe 20 through an insertion port 36 of the hub 22 provided at the proximal end of the probe 20. Inside the hub 22, a proximal end of the drive shaft 21 is rotatably supported, and a rotational force of the scanner motor 35 is transmitted to the drive shaft 21. A signal is transmitted and received between the drive shaft 21 and the diagnostic assistance device 11 via the cable 12. In the diagnostic assistance device 11, a tomographic image of a body lumen is generated and image processing is performed based on the signal transmitted from the drive shaft 21.

The slide unit 32 is mounted with the scanner unit 31 in a manner capable of moving forward and backward, and is mechanically and electrically connected to the scanner unit 31. The slide unit 32 includes a probe clamp unit 37, a slide motor 38, and a switch group 39.

The probe clamp unit 37 is disposed coaxially with the probe connection unit 34 on a distal side of the probe connection unit 34, and supports the probe 20 to be connected to the probe connection unit 34.

The slide motor 38 is a drive source that generates a driving force in the axial direction. The scanner unit 31 moves forward and backward when driven by the slide motor 38, and the drive shaft 21 moves forward and backward in the axial direction accordingly. The slide motor 38 can be, for example, a servo motor.

The switch group 39 can include, for example, a forward switch and a pull-back switch that are pressed when the scanner unit 31 is to be moved forward or backward, and a scan switch that is pressed when image drawing is to be started or ended. Various switches may be included in the switch group 39 as necessary without being limited to the example here.

When the forward switch is pressed, the slide motor 38 rotates forward, and the scanner unit 31 moves forward. On the other hand, when the pull-back switch is pressed, the slide motor 38 rotates backward, and the scanner unit 31 moves backward.

When the scan switch is pressed, the image drawing is started, the scanner motor 35 is driven, and the slide motor 38 is driven to move the scanner unit 31 backward. A user such as an operator connects the probe 20 to the scanner unit 31 in advance, and rotates and moves the drive shaft 21 toward the proximal side in the axial direction upon the start of the image drawing. When the scan switch is pressed again, the scanner motor 35 and the slide motor 38 are stopped, and the image drawing is ended.

The bottom cover 33 covers a bottom and an entire circumference of a side surface on a bottom side of the slide unit 32, and is capable of moving toward and away from the bottom of the slide unit 32.

A configuration of the diagnostic assistance device 11 according to the present embodiment will be described with reference to FIG. 3.

The diagnostic assistance device 11 includes a control unit 41, a storage unit 42, a communication unit 43, an input unit 44, and an output unit 45.

The control unit 41 includes at least one processor, at least one dedicated circuit, or a combination of at least one processor and at least one dedicated circuit. The processor can be a general-purpose processor such as a central processing unit (CPU) or a graphics processing unit (GPU), or a dedicated processor specialized for a specific process. As the dedicated circuit, for example, a field-programmable gate array (FPGA) or an application specific integrated circuit (ASIC) can be used. The control unit 41 executes processing related to an operation of the diagnostic assistance device 11 while controlling each unit of the diagnostic assistance system 10 including the diagnostic assistance device 11.

The storage unit 42 can include at least one semiconductor memory, at least one magnetic memory, at least one optical memory, or a combination of at least two of the at least one semiconductor memory, the at least one magnetic memory, and the at least one optical memory. The semiconductor memory can be, for example, a random access memory (RAM) or a read only memory (ROM). The RAM can be, for example, a static random access memory (SRAM) or a dynamic random access memory (DRAM). The ROM can be, for example, an electrically erasable programmable read only memory (EEPROM). The storage unit 42 functions as, for example, a main storage device, an auxiliary storage device, or a cache memory. The storage unit 42 stores data used for the operation of the diagnostic assistance device 11, such as the tomographic data 51, and data obtained by the operation of the diagnostic assistance device 11, such as the three-dimensional data 52 and the three-dimensional image 53.

The communication unit 43 includes at least one communication interface. The communication interface is a wired local area network (LAN) interface, a wireless LAN interface, or an image diagnostic interface for receiving IVUS signals and performing analog to digital (A/D) conversion on the IVUS signals. The communication unit 43 receives data used for the operation of the diagnostic assistance device 11 and transmits data obtained by the operation of the diagnostic assistance device 11. In the present embodiment, the drive unit 13 is connected to the image diagnostic interface included in the communication unit 43.

The input unit 44 includes at least one input interface. The input interface is, for example, a USB interface, a high-definition multimedia interface (HDMI®) interface, or an interface compatible with short-range wireless communication such as Bluetooth®. The input unit 44 receives an operation of inputting data used for the operation of the diagnostic assistance device 11. In the present embodiment, the keyboard 14 and the mouse 15 are connected to the USB interface or the interface corresponding to short-range wireless communication included in the input unit 44. When a touch screen is provided integrally with the display 16, the display 16 may be connected to the USB interface or the HDMI interface included in the input unit 44.

The output unit 45 includes at least one output interface. The output interface is, for example, a USB interface, an HDMI interface, or an interface compatible with short-range wireless communication such as Bluetooth. The output unit 45 outputs the data obtained by the operation of the diagnostic assistance device 11. In the present embodiment, the display 16 is connected to the USB interface or the HDMI interface included in the output unit 45.

A function of the diagnostic assistance device 11 is implemented by executing a diagnostic assistance program according to the present embodiment by the processor included in the control unit 41. That is, the function of the diagnostic assistance device 11 is implemented by software. The diagnostic assistance program is a program for causing a computer to execute the processing of steps included in the operation of the diagnostic assistance device 11 to implement a function corresponding to the processing of the steps.

That is, the diagnostic assistance program is a program for causing the computer to function as the diagnostic assistance device 11.

The program can be recorded in a computer-readable recording medium. The computer-readable recording medium can be, for example, a magnetic recording device, an optical disc, a magneto-optical recording medium, or a semiconductor memory. The program is distributed by, for example, selling, transferring, or lending a portable recording medium such as a digital versatile disc (DVD) or a compact read only memory (CD-ROM) on which the program is recorded. The program may be distributed by storing the program in a storage of a server and transferring the program from the server to another computer via a network. The program may be provided as a program product.

For example, the computer temporarily stores the program recorded in the portable recording medium or the program transferred from the server in the main storage device. The computer causes the processor to read the program stored in the main storage device, and causes the processor to execute processing according to the read program. The computer may read the program directly from the portable recording medium and execute the processing according to the program. Each time the program is transferred from the server to the computer, the computer may sequentially execute processing according to the received program. The processing may be executed by a so-called application service provider (ASP) type service in which the function is implemented only by execution instruction and result acquisition without transferring the program from the server to the computer. The program includes information provided for processing by an electronic computer and conforming to the program. For example, data that is not a direct command to the computer but has a property that defines the processing of the computer corresponds to the "information conforming to the program".

The functions of the diagnostic assistance device 11 may be partially or entirely implemented by the dedicated circuit included in the control unit 41. That is, the functions of the diagnostic assistance device 11 may be partially or entirely implemented by hardware.

An operation of the diagnostic assistance system 10 according to the present embodiment will be described with reference to FIG. 4. The operation of the diagnostic assistance system 10 corresponds to a diagnostic assistance method according to the present embodiment.

Figure 4:
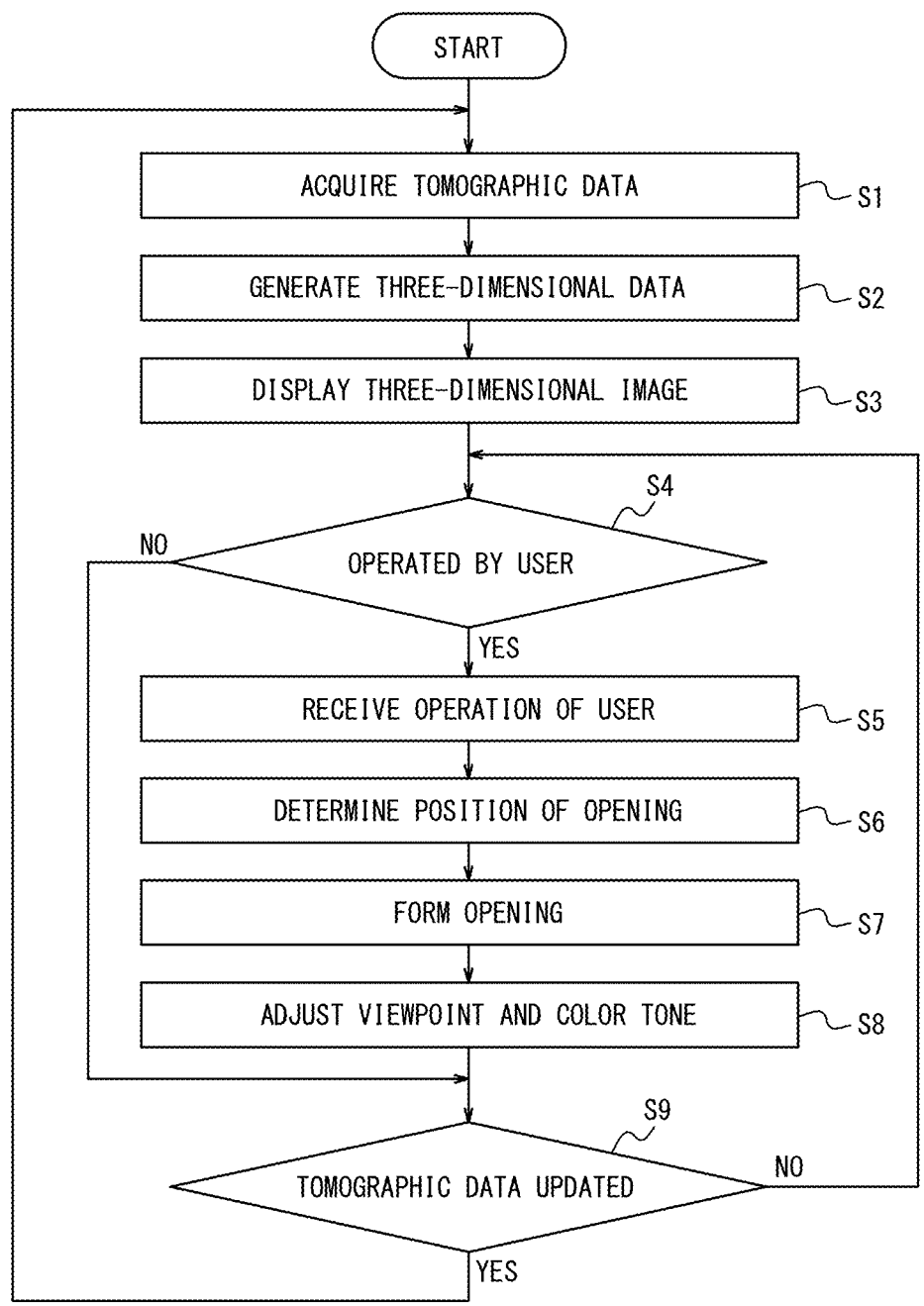
FIG. 4 is a flowchart showing an operation of the diagnostic assistance system according to the embodiment.

Before the start of a flow in FIG. 4, the probe 20 is primed by the user. Thereafter, the probe 20 is fitted into the probe connection unit 34 and the probe clamp unit 37 of the drive unit 13, and is connected and fixed to the drive unit 13. The probe 20 is inserted to a target site in the biological tissue 60 such as the blood vessel or the heart.

In step S1, the scan switch included in the switch group 39 is pressed, and a so-called pull-back operation is performed by pressing the pull-back switch included in the switch group 39. The probe 20 transmits ultrasound inside the biological tissue 60 by the ultrasound transducer 25 that moves backward in the axial direction by the pullback operation. The ultrasound transducer 25 radially transmits the ultrasound while moving inside the biological tissue 60. The ultrasound transducer 25 receives a reflected wave of the transmitted ultrasound. The probe 20 inputs a signal of the reflected wave received by the ultrasound transducer 25 to the diagnostic assistance device 11. The control unit 41 of the diagnostic assistance device 11 processes the input signal to sequentially generate cross-sectional images of the biological tissue 60, thereby acquiring the tomographic data 51, which includes a plurality of cross-sectional images.

Specifically, the probe 20 transmits the ultrasound in a plurality of directions from a rotation center to an outside by the ultrasound transducer 25 while causing the ultrasound transducer 25 to rotate in a circumferential direction and to move in the axial direction inside the biological tissue 60. The probe 20 receives the reflected wave from a reflecting object existing in each of the plurality of directions inside the biological tissue 60 by the ultrasound transducer 25. The probe 20 transmits the signal of the received reflected wave to the diagnostic assistance device 11 via the drive unit 13 and the cable 12. The communication unit 43 of the diagnostic assistance device 11 receives the signal transmitted from the probe 20. The communication unit 43 performs A/D conversion on the received signal. The communication unit 43 inputs the A/D-converted signal to the control unit 41. The control unit 41 processes the input signal to calculate an intensity value distribution of the reflected wave from the reflecting object existing in a transmission direction of the ultrasound of the ultrasound transducer 25. The control unit 41 sequentially generates two-dimensional images having a luminance value distribution corresponding to the calculated intensity value distribution as the cross-sectional images of the biological tissue 60, thereby acquiring the tomographic data 51 which is a data set of the cross-sectional images. The control unit 41 stores the acquired tomographic data 51 in the storage unit 42.

In the present embodiment, the signal of the reflected wave received by the ultrasound transducer 25 corresponds to raw data of the tomographic data 51, and the cross-sectional images generated by processing the signal of the reflected wave by the diagnostic assistance device 11 correspond to processed data of the tomographic data 51.

In a modification of the present embodiment, the control unit 41 of the diagnostic assistance device 11 may store the signal input from the probe 20 as it is in the storage unit 42 as the tomographic data 51. Alternatively, the control unit 41 may store data indicating the intensity value distribution of the reflected wave calculated by processing the signal input from the probe 20 in the storage unit 42 as the tomographic data 51. That is, the tomographic data 51 is not limited to the data set of the cross-sectional images of the biological tissue 60, and may be data representing a cross section of the biological tissue 60 at each moving position of the ultrasound transducer 25 in some format.

In a modification of the present embodiment, an ultrasound transducer that transmits ultrasound in a plurality of directions without rotating may be used instead of the ultrasound transducer 25 that transmits ultrasound in the plurality of directions while rotating in the circumferential direction.

In a modification of the present embodiment, the tomographic data 51 may be acquired using optical frequency domain imaging (OFDI) or optical coherence tomography (OCT) instead of being acquired by using the IVUS. When OFDI or OCT is used, as a sensor that acquires the tomographic data 51 while moving in the biological tissue 60, a sensor that acquires the tomographic data 51 by emitting light in the biological tissue 60 is used instead of the ultrasound transducer 25 that acquires the tomographic data 51 by transmitting the ultrasound in the biological tissue 60.

In a modification of the present embodiment, instead of the diagnostic assistance device 11 generating the data set of the cross-sectional images of the biological tissue 60, another device may generate the same data set, and the diagnostic assistance device 11 may acquire the data set from the other device. That is, instead of the control unit 41 of the diagnostic assistance device 11 processing the IVUS signal to generate the cross-sectional image of the biological tissue 60, another device may process the IVUS signal to generate the cross-sectional image of the biological tissue 60 and input the generated cross-sectional image to the diagnostic assistance device 11.

In step S2, the control unit 41 of the diagnostic assistance device 11 generates the three-dimensional data 52 of the biological tissue 60 based on the tomographic data 51 acquired in step S1.

Specifically, the control unit 41 of the diagnostic assistance device 11 generates the three-dimensional data 52 of the biological tissue 60 by stacking the cross-sectional images of the biological tissue 60 included in the tomographic data 51 stored in the storage unit 42, and converting the same into three-dimensional data. As a method of three-dimensional conversion, any process among a rendering method such as surface rendering or volume rendering, texture mapping accompanying the rendering method, such as environment mapping and bump mapping, or the like is used. The control unit 41 stores the generated three-dimensional data 52 in the storage unit 42.

In step S3, the control unit 41 of the diagnostic assistance device 11 displays the three-dimensional data 52 generated in step S2 on the display 16 as the three-dimensional image 53. At this point, the control unit 41 may arrange, at any position, a viewpoint when displaying the three-dimensional image 53 on the display 16 and virtual light sources 72. The "viewpoint" is a position of a virtual camera 71 as shown in FIG. 5, which is arranged in the three-dimensional space. The number and the relative positions of the light sources 72 are not limited to those illustrated in the drawings, and can be changed as appropriate.

In accordance with an exemplary embodiment, the control unit 41 of the diagnostic assistance device 11 generates the three-dimensional image 53 from the three-dimensional data 52 stored in the storage unit 42. The control unit 41 displays the generated three-dimensional image 53 on the display 16 via the output unit 45.

In step S4, when operated by the user, the processing from step S5 to step S8 is performed. When not operated by the user, the processing from step S5 to step S8 is skipped (or omitted).

Figure 5:
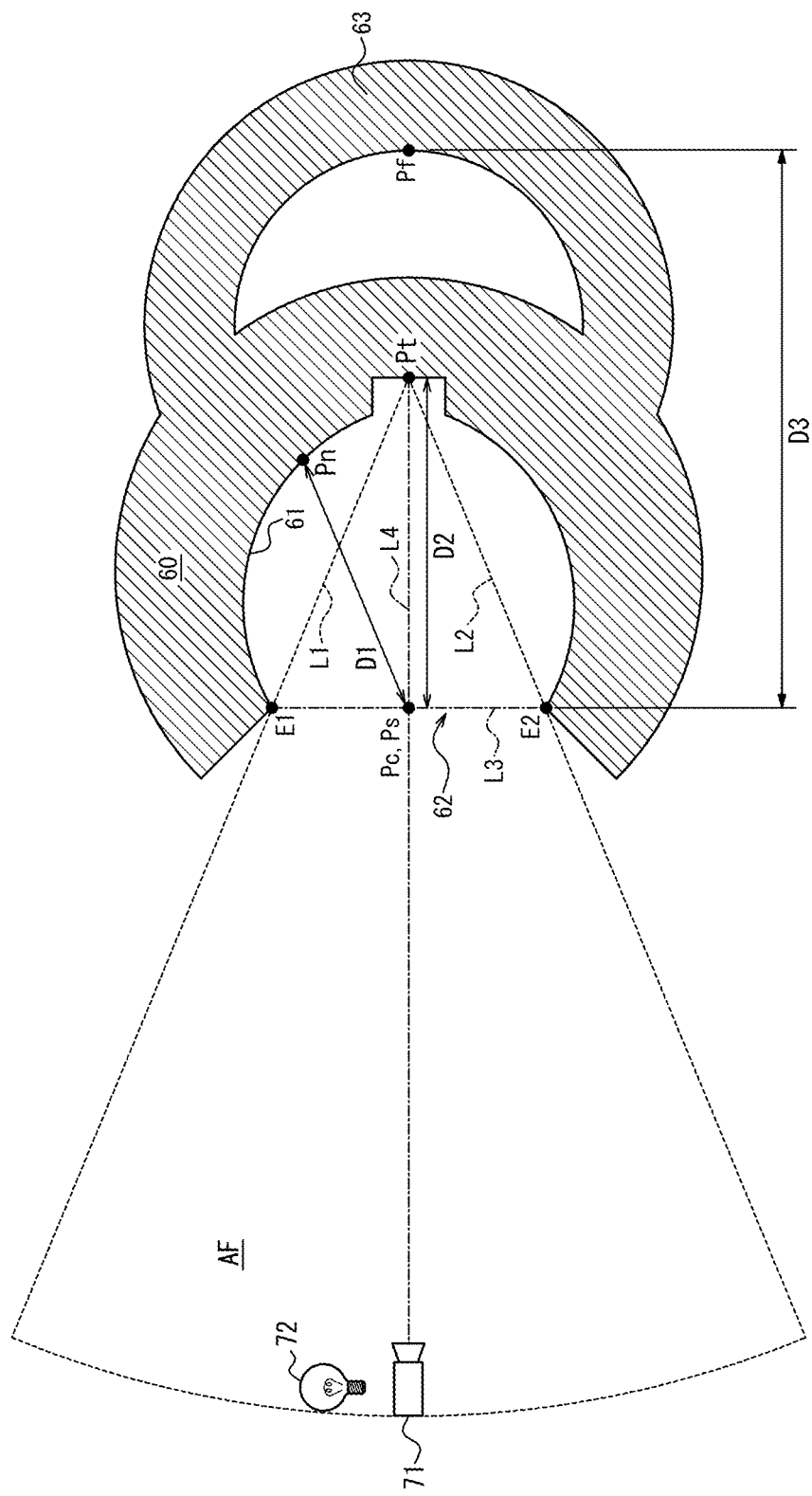
FIG. 5 is a diagram showing a positional relationship between a cross section of a biological tissue, an opening, a viewpoint, and a reference point according to the embodiment.

In step S5, the control unit 41 of the diagnostic assistance device 11 receives, via the input unit 44, an operation of setting a position of the opening 62 as shown in FIG. 5. The position of the opening 62 is set to a position at which an inner wall surface 61 of the biological tissue 60 is exposed to the outside of the biological tissue 60 through the opening 62 in the three-dimensional image 53 displayed in step S3.

Specifically, the control unit 41 of the diagnostic assistance device 11 receives, via the input unit 44, an operation of the user cutting off a portion of the biological tissue 60 using the keyboard 14, the mouse 15, or the touch screen provided integrally with the display 16 in the three-dimensional image 53 displayed on the display 16. In the example of FIG. 5, the control unit 41 receives an operation of cutting off a portion of the biological tissue 60 so that the inner wall surface 61 of the biological tissue 60 has an opened shape in the cross section of the biological tissue 60. The term "cross section of the biological tissue 60" refers to, for example, a tomographic cross section having two end edges of the opening 62 facing each other and the inner wall surface 61 of the biological tissue 60 facing the opening 62, but is not limited to this tomographic cross section, and may be a transverse cross section of the biological tissue 60, a longitudinal cross section of the biological tissue 60, or another cross section of the biological tissue 60. The term "transverse cross section of the biological tissue 60" refers to a cross section obtained by cutting the biological tissue 60 perpendicularly to a direction in which the ultrasound transducer 25 moves in the biological tissue 60. The term "longitudinal cross section of the biological tissue 60" refers to a cross section obtained by cutting the biological tissue 60 along a direction in which the ultrasound transducer 25 moves in the biological tissue 60. The term "another cross section of the biological tissue 60" refers to a cross section obtained by cutting the biological tissue 60 obliquely with respect to a direction in which the ultrasound transducer 25 moves in the biological tissue 60. The term "opened shape" refers to, for example, a substantially C shape, a substantially U shape, a substantially "3" shape, or a shape in which any of these shapes is partially missing due to a hole originally opened in the biological tissue 60, such as a bifurcated portion of the blood vessel or pulmonary vein ostia. In the example of FIG. 5, a shape of the inner wall surface 61 of the biological tissue 60 is a substantially C shape, and a portion facing the opening 62 is missing.

In step S6, the control unit 41 of the diagnostic assistance device 11 determines the position set by the operation received in step S5 as the position of the opening 62.

In accordance with an embodiment, the control unit 41 of the diagnostic assistance device 11 specifies, as three-dimensional coordinates of an edge of the opening 62, three-dimensional coordinates of a boundary of a portion of the biological tissue 60 cut off by the operation of the user in the three-dimensional data 52 stored in the storage unit 42. The control unit 41 stores the specified three-dimensional coordinates in the storage unit 42.

In step S7, the control unit 41 of the diagnostic assistance device 11 forms, in the three-dimensional data 52, the opening 62 that exposes the inner wall surface 61 of the biological tissue 60 to the outside of the biological tissue 60 in the three-dimensional image 53.

In accordance with an embodiment, the control unit 41 of the diagnostic assistance device 11 sets a portion in the three-dimensional data 52 stored in the storage unit 42 that is specified by the three-dimensional coordinates stored in the storage unit 42 to be hidden or transparent when the three-dimensional image 53 is to be displayed on the display 16.

In step S8, the control unit 41 of the diagnostic assistance device 11 adjusts the viewpoint when displaying the three-dimensional image 53 on the display 16 according to the position of the opening 62 formed in step S7. In the present embodiment, the control unit 41 arranges the viewpoint on a straight line extending from the inner wall surface 61 of the biological tissue 60 to the outside of the biological tissue 60 through the opening 62. Therefore, the user can virtually observe the inner wall surface 61 of the biological tissue 60 by looking into the biological tissue 60 through the opening 62.

Specifically, the control unit 41 of the diagnostic assistance device 11 arranges the virtual camera 71 at a position where the inner wall surface 61 of the biological tissue 60 can be seen through the portion set to be hidden or transparent in the three-dimensional image 53 displayed on the display 16. In the example of FIG. 5, the control unit 41 arranges the virtual camera 71 in a region AF sandwiched between a first straight line L1 and a second straight line L2 in the cross section of the biological tissue 60. The first straight line L1 extends from the inner wall surface 61 of the biological tissue 60 to the outside of the biological tissue 60 through a first end edge E1 of the opening 62. The second straight line L2 extends from the inner wall surface 61 of the biological tissue 60 to the outside of the biological tissue 60 through a second end edge E2 of the opening 62. A point at which the first straight line L1 intersects the inner wall surface 61 of the biological tissue 60 is a point Pt identical to a point at which the second straight line L2 intersects the inner wall surface 61 of the biological tissue 60. Therefore, the user can observe the point Pt on the inner wall surface 61 of the biological tissue 60 regardless of a position of the virtual camera 71 in the region AF.

In the example of FIG. 5, the point Pt is identical to a point at which a fourth straight line L4 intersects the inner wall surface 61 of the biological tissue 60. The fourth straight line L4 is drawn perpendicularly to a third straight line L3 from a midpoint Pc of the third straight line L3. The third straight line L3 connects the first end edge E1 of the opening 62 and the second end edge E2 of the opening 62. Therefore, the user can rather easily observe the point Pt on the inner wall surface 61 of the biological tissue 60 through the opening 62. In particular, as shown in FIG. 5, when the virtual camera 71 is arranged on an extension line of the fourth straight line L4, the user can rather easily observe the point Pt on the inner wall surface 61 of the biological tissue 60.

The position of the virtual camera 71 may be any position at which the inner wall surface 61 of the biological tissue 60 can be observed through the opening 62, and is within a range facing the opening 62 in the present embodiment. The position of the virtual camera 71, for example, is preferably set to an intermediate position facing a central portion of the opening 62.

Figure 6:
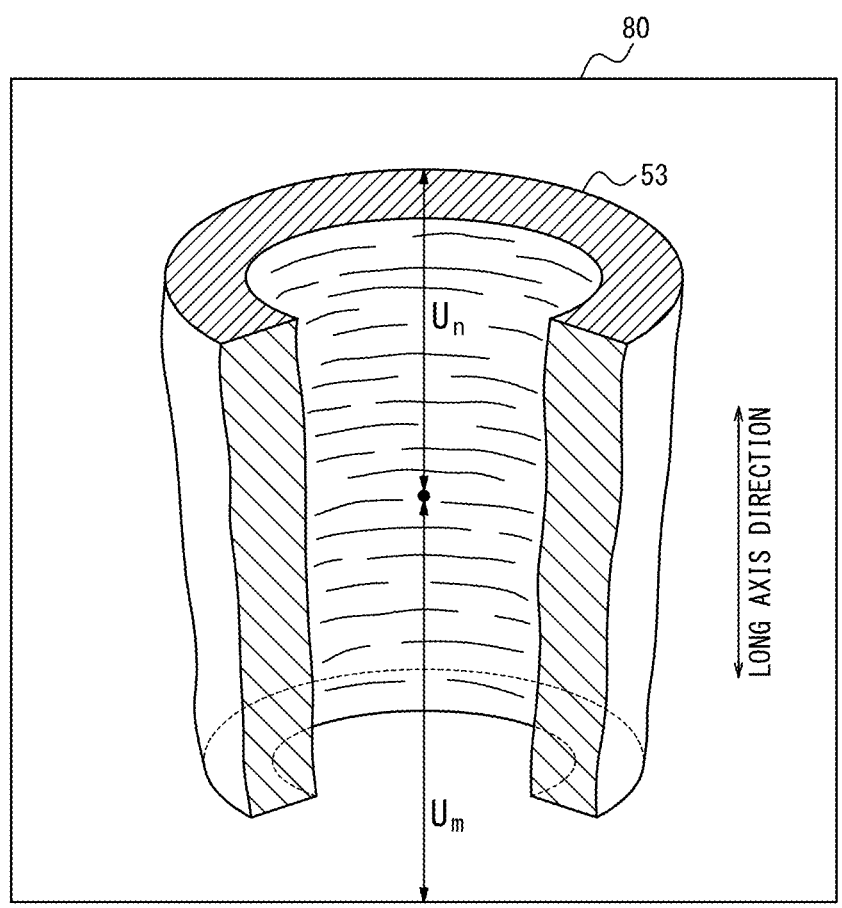
FIG. 6 is a diagram showing a ratio of a size of a three-dimensional image to a screen of a display according to the embodiment.

In the example of FIG. 6, a minimum value Smin and a maximum value Smax are set for a ratio S of a distance Un from a center to one end of the three-dimensional image 53 displayed on a screen 80 of the display 16 to a distance Um from a center to one end of the screen 80 such that the centers of the screen 80 and the three-dimensional image 53 overlap with each other. For example, Smin can be set to ⅓, and Smax can be set to 1. In the example of FIG. 5, a minimum distance from the point Pt to the position of the camera 71 may be set according to the minimum value Sm in, and a maximum distance from the point Pt to the position of the virtual camera 71 may be set according to the maximum value Smax. Alternatively, the minimum distance from the point Pt to the position of the camera 71 may be set to such a distance that the camera 71 is not closer to the point Pt than the opening 62 regardless of the minimum value Sm in. The maximum distance from the point Pt to the position of the virtual camera 71 may be set to such a distance that the camera 71 is not away from the point Pt more than such a distance that the user cannot observe the inner wall surface 61 of the biological tissue 60 regardless of the maximum value Smax.

Furthermore, in step S8, the control unit 41 of the diagnostic assistance device 11 adjusts the color tone of each voxel of the three-dimensional image 53 according to the distance from the reference point Ps in the three-dimensional space to each point of the three-dimensional data 52. The control unit 41 may arrange the reference point Ps at any position, but in the present embodiment, the control unit 41 adjusts a position of the reference point Ps according to the position of the opening 62 formed in step S7.

Specifically, the control unit 41 of the diagnostic assistance device 11 calculates the distance from the reference point Ps in the three-dimensional space to each point of the three-dimensional data 52. The control unit 41 stores, in the storage unit 42, the calculated distance for each point of the three-dimensional data 52. The control unit 41 converts the distance stored in the storage unit 42 into a color tone for each point of the three-dimensional data 52 by using a conversion formula or a conversion table set in advance. The control unit 41 stores, in the storage unit 42, the color tone calculated using the conversion formula or the conversion table for each point of the three-dimensional data 52. The control unit 41 sets a color tone of the corresponding voxel of the three-dimensional image 53 to the color tone stored in the storage unit 42 for each point of the three-dimensional data 52. In the example of FIG. 5, the control unit 41 can arrange the reference point Ps on a straight line in the cross section of the biological tissue 60 that passes through the position of the virtual camera 71 and the midpoint Pc of the third straight line L3. The position of the virtual camera 71 is the viewpoint when the three-dimensional image 53 is displayed on the display 16. The third straight line L3 connects the first end edge E1 of the opening 62 and the second end edge E2 of the opening 62. Therefore, since the positions of the viewpoint, the reference point Ps, and the midpoint Pc in a left-right direction are aligned, when the user observes the inner wall surface 61 of the biological tissue 60 through the opening 62, the unevenness and depth can be rather easily grasped by the difference in color tone of the three-dimensional image 53. In particular, as shown in FIG. 5, when the reference point Ps is arranged on the fourth straight line L4, the user can rather easily grasp the point Pt of the inner wall surface 61 of the biological tissue 60 and the unevenness and depth around the point Pt. In the example of FIG. 5, the reference point Ps is arranged at the same position as the midpoint Pc.

In step S9, when the tomographic data 51 is updated, the processing of step S1 and the subsequent steps are performed again. When the tomographic data 51 is not updated, the step of whether operated by the user is confirmed again in step S4.

In steps S5 to S8 for the second and subsequent times, when the position of the opening 62 is changed from a first position to a second position, the control unit 41 of the diagnostic assistance device 11 moves the viewpoint from a third position corresponding to the first position to a fourth position corresponding to the second position. The control unit 41 moves the virtual light sources 72 when the three-dimensional image 53 is to be displayed on the display 16, in accordance with movement of the viewpoint from the third position to the fourth position.

The control unit 41 moves the virtual light sources 72 by using a rotation matrix used for moving the virtual camera 71 when changing the position of the opening 62 in the circumferential direction in the cross section of the biological tissue 60.

The control unit 41 may instantly switch the viewpoint from the third position to the fourth position when changing the position of the opening 62 from the first position to the second position, but in the present embodiment, a video in which the viewpoint gradually moves from the third position to the fourth position is displayed on the display 16 as the three-dimensional image 53. Therefore, the movement of the viewpoint can be easily introduced to the user.

In a modification of the present embodiment, in step S5, the control unit 41 of the diagnostic assistance device 11 may receive, via the input unit 44, an operation of setting a position of a target point that the user wants to see and an operation of setting the position of the opening 62.

Specifically, in the three-dimensional image 53 displayed on the display 16, the control unit 41 of the diagnostic assistance device 11 may receive, via the input unit 44, an operation of designating the position of the target point using the keyboard 14, the mouse 15, or the touch screen provided integrally with the display 16 by the user. In the example of FIG. 5, the control unit 41 may receive, via the input unit 44, an operation of setting a position of the point Pt as a position of the point at which the first straight line L1 and the second straight line L2 intersect the inner wall surface 61 of the biological tissue 60.

In a modification of the present embodiment, in step S5, the control unit 41 of the diagnostic assistance device 11 may receive, via the input unit 44, an operation of setting the position of the target point that the user wants to see, instead of the operation of setting the position of the opening 62. In step S6, the control unit 41 may determine the position of the opening 62 according to the position set by the operation received in step S5.

Specifically, in the three-dimensional image 53 displayed on the display 16, the control unit 41 of the diagnostic assistance device 11 may receive, via the input unit 44, the operation of designating the position of the target point using the keyboard 14, the mouse 15, or the touch screen provided integrally with the display 16 by the user. The control unit 41 may determine the position of the opening 62 according to the position of the target point. In the example of FIG. 5, the control unit 41 may receive, via the input unit 44, an operation of setting the position of the point Pt as the position of the point at which the first straight line L1 and the second straight line L2 intersect the inner wall surface 61 of the biological tissue 60. In the cross section of the biological tissue 60, the control unit 41 may determine, as the region AF, a fan-shaped region centered on the point Pt and having a central angle that can be preset or that is an angle specified by the user. The control unit 41 may determine a position in the biological tissue 60 that overlaps with the region AF as the position of the opening 62. The control unit 41 may determine a normal line of the inner wall surface 61 of the biological tissue 60 perpendicular to a tangent line passing through the point Pt as the fourth straight line L4.

The region AF may be set to be narrower than a width of the opening 62. That is, the region AF may be set so as not to include at least one of the first end edge E1 of the opening 62 and the second end edge E2 of the opening 62.

In a modification of the present embodiment, the point at which the first straight line L1 intersects the inner wall surface 61 of the biological tissue 60 may not be identical to the point at which the second straight line L2 intersects the inner wall surface 61 of the biological tissue 60. For example, a point P1 at which the first straight line L1 intersects the inner wall surface 61 of the biological tissue 60 and a point P2 at which the second straight line L2 intersects the inner wall surface 61 of the biological tissue 60 may be on a circumference centered on the point Pt. That is, the point P1 and the point P2 may be substantially equidistant from the point Pt.

In a modification of the present embodiment, in step S8, when at least a part of a point group in the three-dimensional data 52 in a range to be displayed on the display 16 as the three-dimensional image 53 has a difference in color tone with respect to a difference in a distance from the reference point Ps that does not satisfy a condition, the control unit 41 of the diagnostic assistance device 11 may correct the color tone of each voxel of the three-dimensional image 53 in accordance with the condition.

Figure 7A:
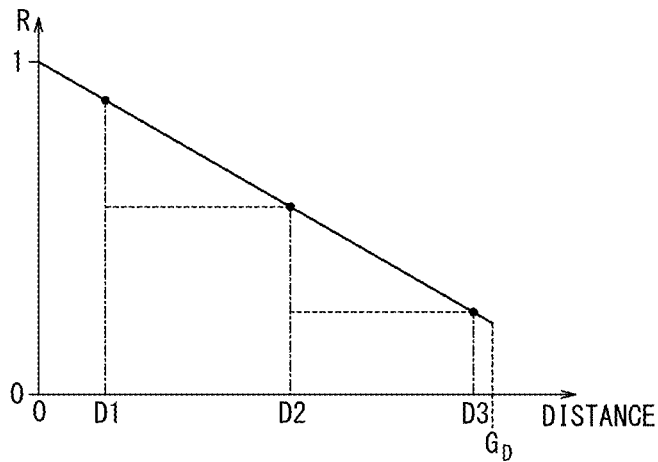
FIG. 7A is a graph showing a relationship between a distance from the reference point in three-dimensional data and an R value in the three-dimensional image according to the embodiment.
Figure 7B:
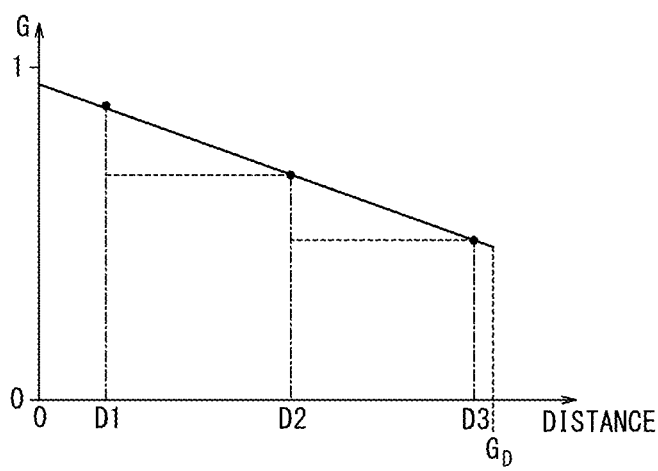
FIG. 7B is a graph showing a relationship between the distance from the reference point in the three-dimensional data and a G value in the three-dimensional image according to the embodiment.
Figure 7C:
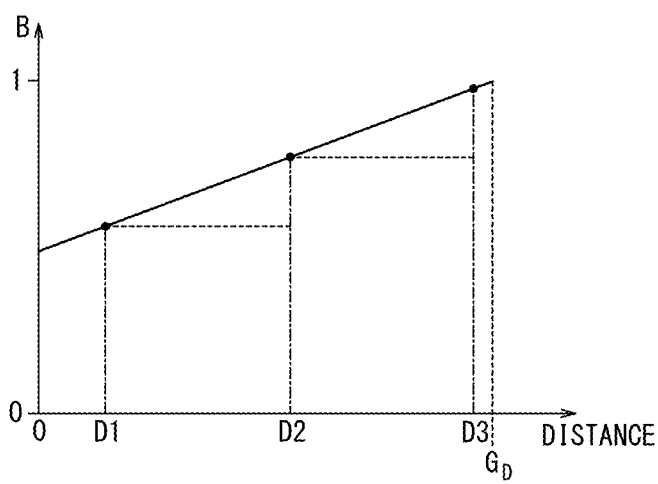
FIG. 7C is a graph showing a relationship between the distance from the reference point in the three-dimensional data and a B value in the three-dimensional image according to the embodiment.

In accordance with an embodiment, the control unit 41 of the diagnostic assistance device 11 analyzes a relationship between the distance from the reference point Ps stored in the storage unit 42 and the color tone calculated using the conversion formula or the conversion table stored in the storage unit 42, for a point group in a range that can be observed through the opening 62 among a point group of the three-dimensional data 52. The control unit 41 specifies a relationship between the distance and RGB values as shown in FIGS. 7A, 7B, and 7C as an analysis result. For example, as shown in FIGS. 5 and 7A to 7C, it can be assumed that a ratio of the difference in color tone to the difference between a distance D1 from the reference point Ps to a point Pn and a distance D2 from the reference point Ps to the point Pt is less than a ratio Rt set as a condition. Alternatively, as shown in FIGS. 5 and 7A to 7C, it is assumed that a ratio of the difference in color tone to the difference between the distance D2 from the reference point Ps to the point Pt and a distance D3 from the reference point Ps to a point Pf is less than the ratio Rt set as a condition. In this case, the control unit 41 corrects the color tone of the point group in the range that can be observed through the opening 62 among the point group of the three-dimensional data 52 such that a slope of a graph as shown in each of FIGS. 7A to 7C increases. In the example of FIG. 5, the point Pt is located at a center inside a concave portion of the inner wall surface 61 of the biological tissue 60 facing the opening 62. The point Pn is located outside the concave portion of the inner wall surface 61 of the biological tissue 60. The point Pf is on an inner wall surface of an expanding portion 63 on a side opposite to the opening 62 with respect to the concave portion of the biological tissue 60. The expanding portion 63 is formed by expanding a portion of the biological tissue 60 in a long axis direction (axial direction) that does not include the point Pt. Therefore, even from the position of the virtual camera 71, the inner wall surface of the expanding portion 63 can be observed diagonally through the opening 62 so as to avoid the point Pt of the inner wall surface 61 of the biological tissue 60 and the periphery of the point Pt. The ratio Rt can be, for example, preferably set such that the difference in color tone with respect to the difference between the distance D1 and the distance D2 is a difference in color tone that can be recognized by humans. The ratio Rt can be, for example, more preferably set such that the difference in color tone with respect to the difference between the distance D2 and the distance D3 is a difference in color tone that can be recognized by humans. As the analysis result, the control unit 41 may specify a relationship between the distance and a value related to the other color tones, such as a relationship between the distance and the brightness, or a relationship between the distance and the saturation, instead of specifying the relationship between the distance and the RGB value.

In a modification of the present embodiment, in step S5, the control unit 41 of the diagnostic assistance device 11 may receive, via the input unit 44, an operation of changing a difference in color tone with respect to a difference in a distance from the reference point Ps of at least a part of the point group in the three-dimensional data 52 in the range to be displayed on the display 16 as the three-dimensional image 53. In step S8, the control unit 41 may change the color tone of each voxel of the three-dimensional image 53 in response to the operation received in step S5.

Specifically, the control unit 41 of the diagnostic assistance device 11 may receive, via the input unit 44, the operation of changing the difference in color tone with respect to the difference in the distance from the reference point Ps using the keyboard 14, the mouse 15, or the touch screen provided integrally with the display 16 by the user. In the example of FIGS. 7A to 7C, the control unit 41 may display graphs of FIGS. 7A to 7C on the display 16 and receive an operation of changing slopes of the graphs via the input unit 44. The control unit 41 changes the color tone of the corresponding voxel of the three-dimensional image 53 for each point of the three-dimensional data 52 such that the slopes of the graphs shown in FIGS. 7A to 7C have a magnitude corresponding to the received operation.

In a modification of the present embodiment, in step S5, the control unit 41 of the diagnostic assistance device 11 may receive, via the input unit 44, an operation of changing the position of the reference point Ps. In step S8, the control unit 41 may change the color tone of each voxel of the three-dimensional image 53 in response to the operation received in step S5.

In accordance with an exemplary embodiment, in the three-dimensional image 53 displayed on the display 16, the control unit 41 of the diagnostic assistance device 11 may receive, via the input unit 44, the operation of changing the position of the reference point Ps using the keyboard 14, the mouse 15, or the touch screen provided integrally with the display 16 by the user. In that case, the control unit 41 calculates a distance from the changed reference point Ps to each point of the three-dimensional data 52. The control unit 41 stores, in the storage unit 42, the calculated distance for each point of the three-dimensional data 52. The control unit 41 converts the distance stored in the storage unit 42 into the color tone for each point of the three-dimensional data 52 by using the conversion formula or the conversion table set in advance. The control unit 41 stores, in the storage unit 42, the color tone calculated using the conversion formula or the conversion table for each point of the three-dimensional data 52. The control unit 41 changes the color tone of the corresponding voxel of the three-dimensional image 53 to the color tone stored in the storage unit 42 for each point of the three-dimensional data 52.

Figure 8:
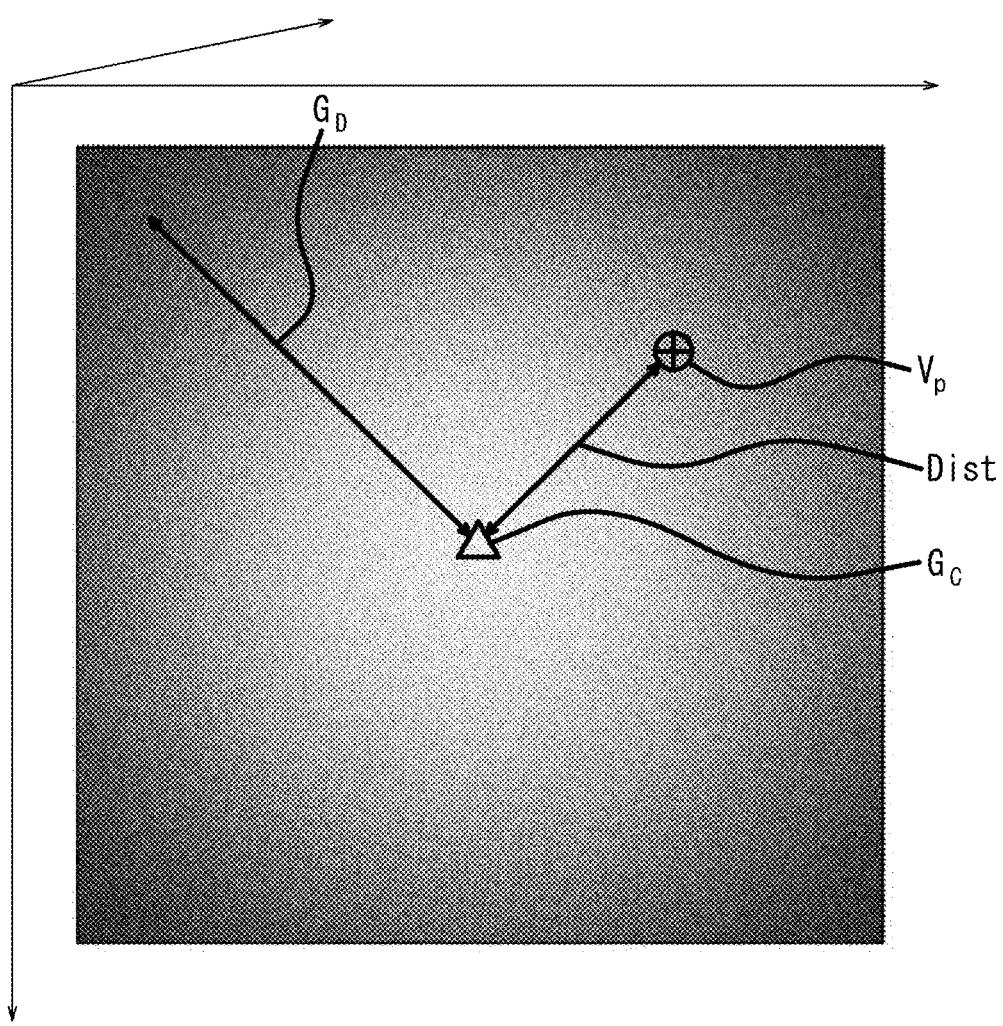
FIG. 8 is a diagram showing a gradation according to the embodiment.
Figure 9:
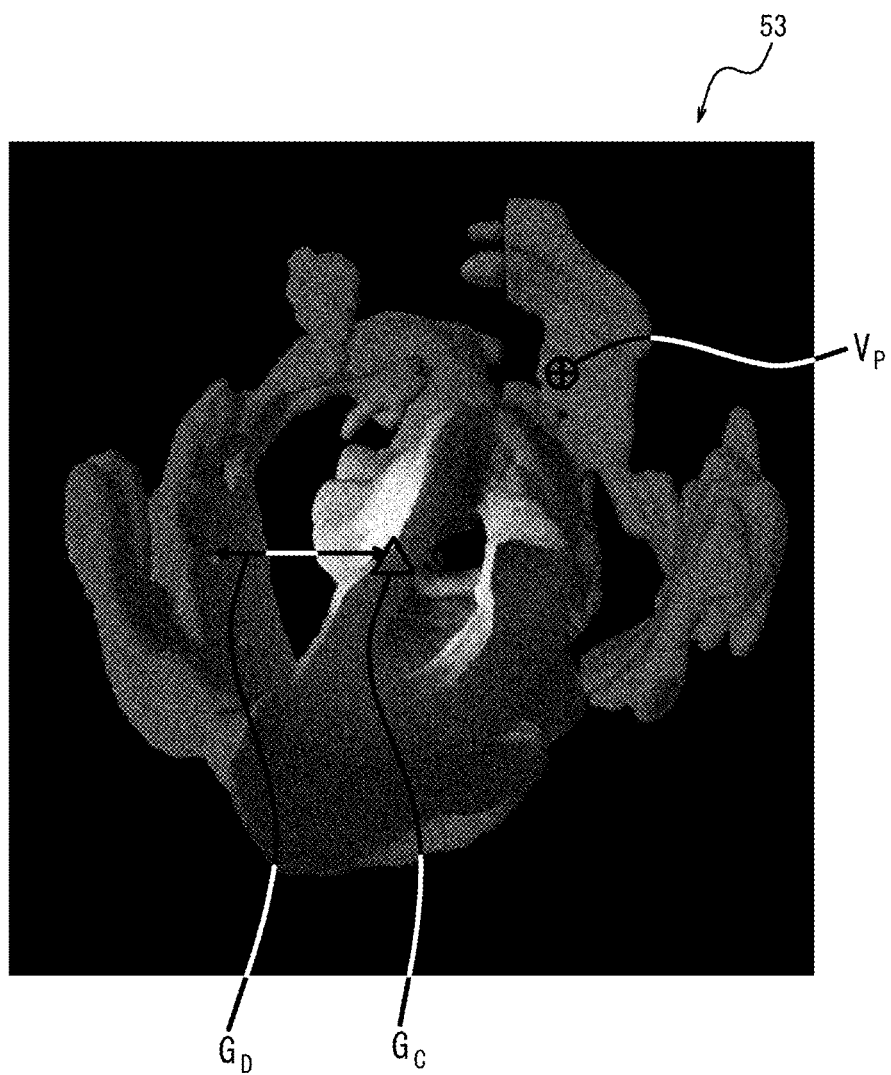
FIG. 9 is a diagram showing a gradation according to the embodiment.

In the present embodiment, the control unit 41 of the diagnostic assistance device 11 can adjust the color tone of each voxel of the three-dimensional image 53 according to the distance from the reference point Ps in the three-dimensional space to each point of the three-dimensional data 52, thereby forming a gradation that changes radially in a three-dimensional manner from the reference point Ps in the three-dimensional image 53 as shown in FIGS. 8 and 9.

In the example of FIGS. 8 and 9, $G_C$ is a center point of the gradation, $G_D$ is a distance from $G_C$ to a gradation edge, $G_{NEAR}$ is a color at $G_C$, and $G_{FAR}$ is a color at a position separated by $G_D$ from $G_C$. The "gradation edge" is an outer edge of a range applied with the gradation. $V_P$ is any visible voxel information in the three-dimensional data 52. The "visible voxel information" refers to voxel information in which the biological tissue 60 is present in the three-dimensional data 52. Dist is a distance between $V_P$ and $G_C$, and $Color_P$ is a color of $V_P$. $G_{NEAR}$, $G_{FAR}$, and $Color_P$ are RGB values. $G_{NEAR}$ and $G_{FAR}$ in this example are specifically shown below, with maximum values of red, green, and blue in RGB values each being 1.

$$G_{NEAR}=(1.00,0.95,0.48)$$

$$G_{FAR}=(0.20,0.47,1.00)$$

The control unit 41 sets the color tone of each voxel of the three-dimensional image 53 by the following calculation.

$$\text{Dist}=\text{distance}(V_P,G_c)$$

$$Clr_F=\text{clamp}(\text{Dist}/G_D,0,1)$$

$$Color_P=G_{NEAR}\times(1-Clr_F)+G_{FAR}\times Clr_F$$

Here, distance( ) is a function for calculating the distance, and clamp( ) is a clamp function.

In the example of FIGS. 5, 7A to 7C, and 8, the reference point Ps corresponds to $G_C$, the point Pn, the point Pt, and the point Pf correspond to $V_P$, and the distance D1, the distance D2, and the distance D3 correspond to Dist.

As a specific example, it is assumed that $G_C$, $V_P$, and $G_D$ are set as follows.

$$G_C=(0.5,0.5,0.5)$$

$$V_P=(0.4,0.4,0.25)$$

$$G_D=0.3$$

In this case, Dist, $Clr_F$, and $Color_P$ can be obtained as follows.

$$\text{Dist}=\text{distance}(V_P,G_C)=\sqrt{((0.5-0.4)^2+(0.5-0.4)^2+(0.5-0.25)^2)}=0.29$$

$$Clr_F=\text{clamp}(\text{Dist}/G_D,0,1)=0.29/0.3=0.96$$

$$Color_P=G_{NEAR}\times(1-Clr_F)+G_{FAR}\times Clr_F=(1.00,0.95,0.48)\times0.04+(0.20,0.47,1.00)\times0.96=(0.23,0.49,0.98)$$

Figure 10:
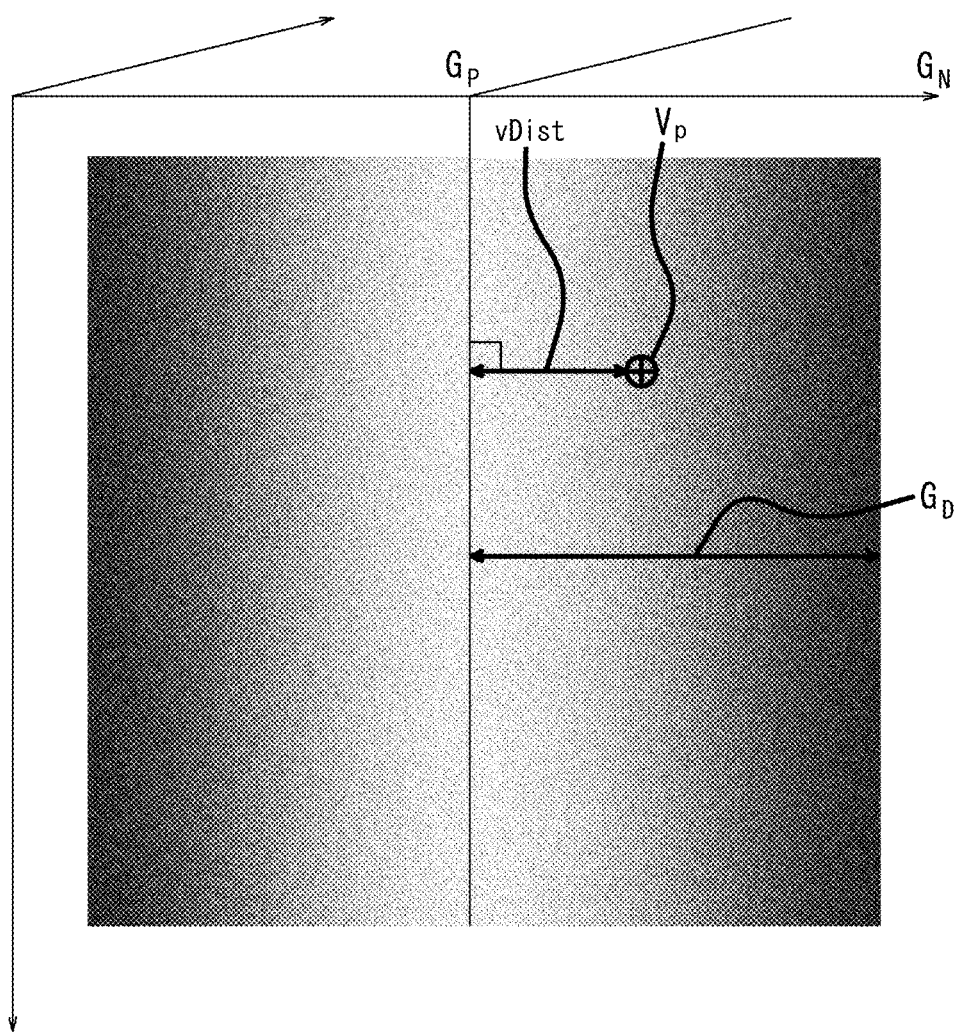
FIG. 10 is a diagram showing a gradation according to a modification.
Figure 11:
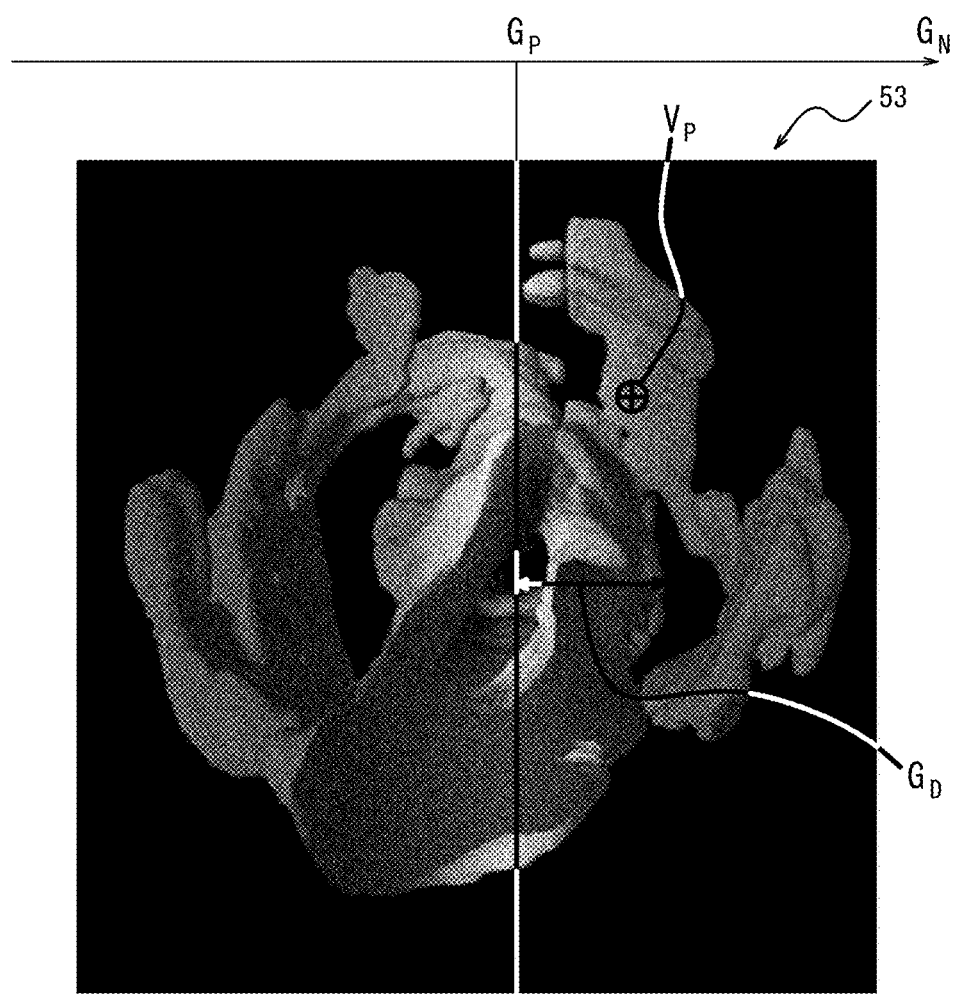
FIG. 11 is a diagram showing a gradation according to the modification.

In a modification of the present embodiment, the control unit 41 of the diagnostic assistance device 11 may adjust the color tone of each voxel of the three-dimensional image 53 according to a distance from a reference plane in the three-dimensional space to each point of the three-dimensional data 52, thereby forming a gradation that changes in layers from the reference plane in the three-dimensional image 53 as shown in FIGS. 10 and 11.

In the example of FIGS. 10 and 11, GN is a gradation direction, $G_P$ is a gradation plane position, $G_D$ is a distance from $G_P$ to a gradation edge, $G_{NEAR}$ is a color at $G_P$, and $G_{FAR}$ is a color at a position separated by $G_D$ from $G_P$ to GN. GN is a direction perpendicular to $G_P$. $V_P$ is any visible voxel information in the three-dimensional data 52. vDist is a distance between $V_P$ and $G_P$, and $Color_P$ is the color of $V_P$. $G_{NEAR}$, $G_{FAR}$, and $Color_P$ are RGB values. $G_{NEAR}$ and $G_{FAR}$ in this example are the same as those in FIGS. 8 and 9.

The control unit 41 sets the color tone of each voxel of the three-dimensional image 53 by the following calculation.

$$v\text{Dist}=v\text{distance}(V_P,G_P)$$

$$Clr_F=\text{clamp}(v\text{Dist}/G_D,0,1)$$

$$Color_P=G_{NEAR}\times(1-Clr_F)+G_{FAR}\times Clr_F$$

Here, vdistance( ) is a function that calculates a length of a perpendicular line drawn from $V_P$ to $G_P$ as a distance. In the three-dimensional space, when GN is in a Y axis direction, $G_P$ is a plane parallel to an XZ plane, and vDist is an absolute value of a difference between y components of $V_P$ and $G_P$.

As a specific example, it is assumed that the reference plane is a plane parallel to a Y axis, and $G_P$, $V_P$, and $G_D$ are set as follows.

$$G_P=(0.5)$$

$$V_P=(0.35,0.7,0.0)$$

$$G_D=0.3$$

In this case, vDist, $Clr_F$, and $Color_P$ can be obtained as follows.

$$v\text{Dist}=v\text{distance}(V_P,G_P)=|0.5-0.7|=0.2$$

$$Clr_F=\text{clamp}(v\text{Dist}/G_D,0,1)=0.2/0.3=0.67$$

$Color_P=G_{NEAR}\times(1-Clr_F)+G_{FAR}\times Clr_F=(1.00,0.95,0.48)\times0.33+(0.20,0.47,1.00)\times0.67=(0.46,0.63,0.83)$ In step S8, the control unit 41 of the diagnostic assistance device 11 may adjust a position of the reference plane according to the position of the opening 62 formed in step S7.

In step S8, when at least a part of the point group in the three-dimensional data 52 in the range to be displayed on the display 16 as the three-dimensional image 53 has a difference in color tone with respect to a difference in a distance from the reference plane that does not satisfy a condition, the control unit 41 of the diagnostic assistance device 11 may correct the color tone of each voxel of the three-dimensional image 53 in accordance with the condition.

In step S5, the control unit 41 of the diagnostic assistance device 11 may receive, via the input unit 44, an operation of changing the difference in color tone with respect to the difference in the distance from the reference plane of at least a part of the point group in the three-dimensional data 52 in the range to be displayed on the display 16 as the three-dimensional image 53. In step S8, the control unit 41 may change the color tone of each voxel of the three-dimensional image 53 in response to the operation received in step S5.

In step S5, the control unit 41 of the diagnostic assistance device 11 may receive, via the input unit 44, an operation of changing the position of the reference plane. In step S8, the control unit 41 may change the color tone of each voxel of the three-dimensional image 53 in response to the operation received in step S5.

Figure 12:
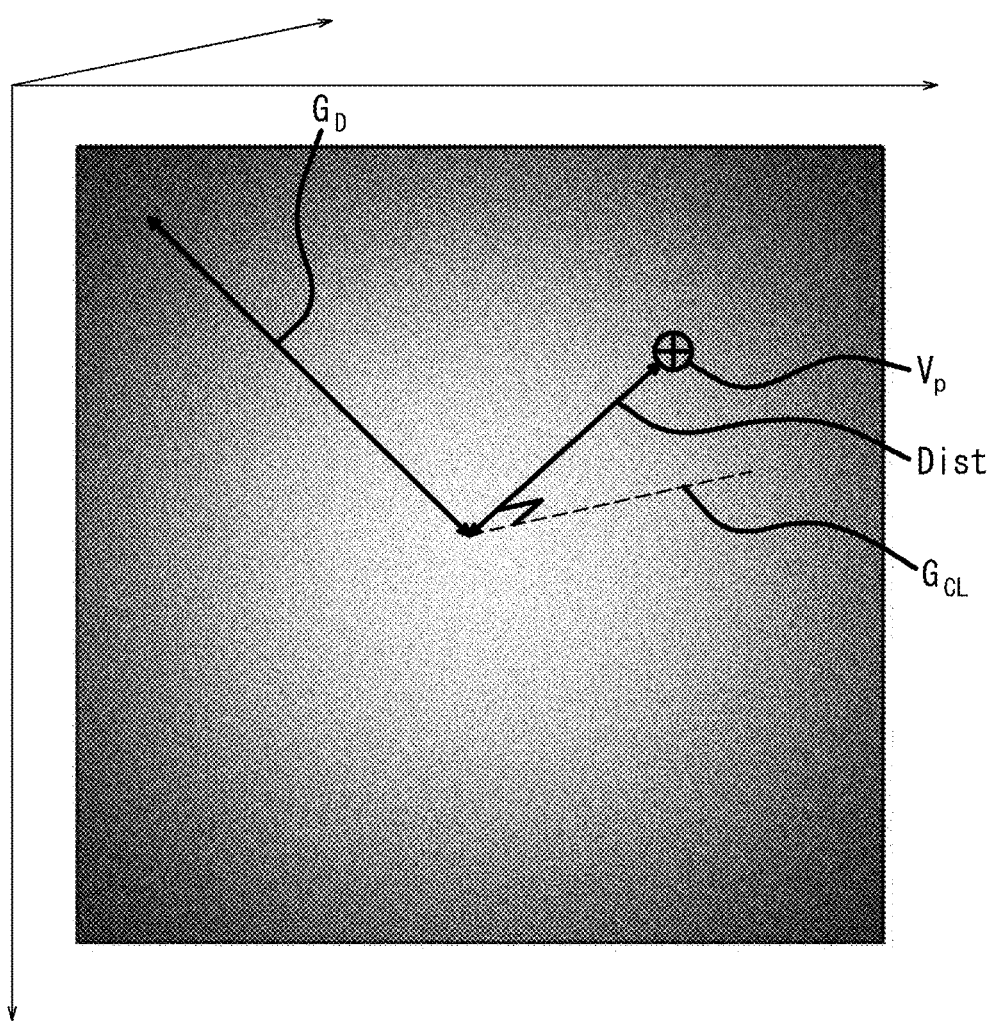
FIG. 12 is a diagram showing a gradation according to the modification.

In a modification of the present embodiment, the control unit 41 of the diagnostic assistance device 11 adjusts the color tone of each voxel of the three-dimensional image 53 according to a distance from a reference line in the three-dimensional space to each point of the three-dimensional data 52, thereby forming a gradation that changes radially in a two-dimensional manner from the reference line in the three-dimensional image 53 as shown in FIG. 12.

In the example of FIG. 12, $G_{CL}$ is a centerline of a gradation, $G_D$ is a distance from $G_{CL}$ to a gradation edge, $G_{NEAR}$ is a color at $G_{CL}$, and $G_{FAR}$ is a color at a position separated by $G_D$ from $G_{CL}$ in a perpendicular direction. $V_P$ is any visible voxel information in the three-dimensional data 52. vDist is a distance between $V_P$ and $G_{CL}$, and $Color_P$ is the color of $V_P$. $G_{NEAR}$, $G_{FAR}$, and $Color_P$ are RGB values. $G_{NEAR}$ and $G_{FAR}$ in this example are the same as those in FIGS. 8 and 9, and FIGS. 10 and 11.

The control unit 41 sets the color tone of each voxel of the three-dimensional image 53 by the following calculation.

$vDist=vdistance(V_P, G_{CL})$ $Clr_F=clamp(vDist/G_D, 0, 1)$ $Color_P=G_{NEAR}\times(1-Clr_F)+G_{FAR}\times Clr_F$ Here, vdistance( ) is a function for calculating a length of a perpendicular line drawn from $V_P$ to $G_{CL}$ as a distance. $G_{CL}$ can be set as any line. For example, $G_{CL}$ may be a straight line parallel to the Z axis in the three-dimensional space, may be a line connecting a center of gravity of the biological tissue 60 along an extending direction of the tubular biological tissue 60, or may be an axis line of the probe 20.

As a specific example, it is assumed that the reference line is a straight line parallel to the Z axis, and $G_{CL}$, $V_P$, and $G_D$ are set as follows.

$G_P=(0.5,0.5)$ $V_P=(0.5,0.55,0.5)$ $G_D=0.3$

In this case, vDist, $Clr_F$, and $Color_P$ can be obtained as follows.

$vDist=vdistance(V_P, G_{CL})=\sqrt{((0.5-0.5)^2+(0.5-0.55)^2)}=0.05$ $Clr_F=clamp(vDist/G_D, 0, 1)=0.05/0.3=0.17$ $Color_P=G_{NEAR}\times(1-Clr_P)+G_{FAR}\times Clr_P=(1.00,0.95,0.48)\times0.83+(0.20,0.47,1.00)\times0.17=(0.86,0.86,0.57)$ In step S8, the control unit 41 of the diagnostic assistance device 11 may adjust a position of the reference line according to the position of the opening 62 formed in step S7.

In step S8, when at least a part of the point group in the three-dimensional data 52 in the range to be displayed on the display 16 as the three-dimensional image 53 has a difference in color tone with respect to a difference in a distance from the reference line that does not satisfy a condition, the control unit 41 of the diagnostic assistance device 11 may correct the color tone of each voxel of the three-dimensional image 53 in accordance with the condition.

In step S5, the control unit 41 of the diagnostic assistance device 11 may receive, via the input unit 44, an operation of changing the difference in color tone with respect to the difference in the distance from the reference line of at least a part of the point group in the three-dimensional data 52 in the range to be displayed on the display 16 as the three-dimensional image 53. In step S8, the control unit 41 may change the color tone of each voxel of the three-dimensional image 53 in response to the operation received in step S5.

In step S5, the control unit 41 of the diagnostic assistance device 11 receives, via the input unit 44, an operation of changing the position of the reference line. In step S8, the control unit 41 may change the color tone of each voxel of the three-dimensional image 53 in response to the operation received in step S5.

As described above, in the present embodiment, the control unit 41 of the diagnostic assistance device 11 generates the three-dimensional data 52 of the biological tissue 60 based on the tomographic data 51 of the biological tissue 60. The control unit 41 displays the generated three-dimensional data 52 as the three-dimensional image 53 on the display 16. The control unit 41 adjusts the color tone of each voxel of the three-dimensional image 53 according to the distance from the reference point Ps in the three-dimensional space to each point of the three-dimensional data 52.

According to the present embodiment, it can be rather easy for a user to grasp unevenness or depth in the three-dimensional space. For example, when the user is an operator, it can be rather easy to grasp the shape of the biological tissue 60, which facilitates treatment.

In the present embodiment, once the position of the opening 62 is determined, the positions of the camera 71 and the light sources 72 move such that the inside of the biological tissue 60 can be seen from the opening 62. Therefore, when the position of the opening 62 is changed to another position, it is possible to avoid a situation that only the outer wall surface of the biological tissue 60 can be seen and an object of interest cannot be confirmed.

According to the present embodiment, the unevenness in the three-dimensional space can be expressed. The depth in the three-dimensional space can be expressed. When the position of the opening 62 is changed and the positions of the camera 71 and the light sources 72 are changed, the color tone is also changed in accordance with the change, and thus the unevenness can be rather easily expressed.

In the present embodiment, since the color tone is changed according to the distance from the reference point Ps, it is relatively easy to grasp the unevenness or the depth.

In the present embodiment, the reference point Ps is automatically changed every time the position of the opening 62 is changed, so that the usefulness of the diagnostic assistance system 10 is improved.

The present disclosure is not limited to the above-described embodiment. For example, a plurality of blocks described in a block diagram may be integrated, or one block may be divided. Instead of executing a plurality of steps described in a flowchart in time series according to the description, the steps may be executed in parallel or in a different order according to the processing capability of the device that executes each step or as necessary. In addition, modifications can be made without departing from a gist of the present disclosure.

For example, a method for setting the color tone of each voxel of the three-dimensional image 53 in the control unit 41 may be not only calculation based on the RGB values described above, but also calculation based on another index for expressing color, such as an ARGB value including transparency in the RGB values.

The detailed description above describes embodiments of a diagnostic assistance device, a diagnostic assistance system, and a diagnostic assistance method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnostic assistance device configured to generate three-dimensional data of a biological tissue based on tomographic data of the biological tissue, and display the generated three-dimensional data as a three-dimensional image on a display, the diagnostic assistance device comprising:
   a processor configured to adjust a color tone of each voxel of the three-dimensional image according to a distance from a reference point, a reference line, or a reference plane in a three-dimensional space to each point of the three-dimensional data,
   wherein the processor is configured to form, in the three-dimensional data, an opening that exposes an inner wall surface of the biological tissue to an outside of the biological tissue in the three-dimensional image, and adjust a position of the reference point, the reference line, or the reference plane according to a position of the formed opening.

2. The diagnostic assistance device according to claim 1, wherein the processor is configured to arrange the reference point on a straight line in a cross section of the biological tissue that passes through a viewpoint when the three-dimensional image is displayed on the display and a midpoint of a straight line connecting a first end edge of the opening and a second end edge of the opening.

3. The diagnostic assistance device according to claim 1, wherein the processor is configured to arrange the reference point on a straight line drawn perpendicularly to a straight line connecting a first end edge of the opening and a second end edge of the opening from a midpoint of the straight line.

4. The diagnostic assistance device according to claim 1, wherein the processor is configured to receive an operation of changing a difference in color tone with respect to a difference in distance from the reference point, the reference line, or the reference plane of at least a part of a point group in the three-dimensional data in a range to be displayed on the display as the three-dimensional image, and change the color tone of each voxel of the three-dimensional image in response to the received operation.

5. The diagnostic assistance device according to claim 1, wherein the processor is configured to receive an operation of changing a position of the reference point, the reference line, or the reference plane, and change the color tone of each voxel of the three-dimensional image in response to the received operation.

6. A diagnostic assistance device configured to generate three-dimensional data of a biological tissue based on tomographic data of the biological tissue, and display the generated three-dimensional data as a three-dimensional image on a display, the diagnostic assistance device comprising:
   a processor configured to adjust a color tone of each voxel of the three-dimensional image according to a distance from a reference point, a reference line, or a reference plane in a three-dimensional space to each point of the three-dimensional data,
   wherein the processor is configured to:
      convert the distance from the reference point, the reference line, or the reference plane to each point of the three-dimensional data into a color tone for each point of the three-dimensional data by using a conversion formula or a conversion table set in advance;
      analyze a relationship between the distance from the reference point, the reference line, or the reference plane to each point of the three-dimensional data and the color tone for each point of the three-dimensional data, for a point group in a predetermined range among a point group of the three-dimensional data; and
      correct a color tone of the point group in the predetermined range when a ratio of a difference in color tone to a difference between a distance from the reference point, the reference line, or the reference plane to a first point and a distance from the reference point, the reference line, or the reference plane to a second point is less than a ratio set as a condition, the first and second points being included in the point group in the predetermined range.

7. A diagnostic assistance device configured to generate three-dimensional data of a biological tissue based on tomographic data of the biological tissue, and display the generated three-dimensional data as a three-dimensional image on a display, the diagnostic assistance device comprising:
   a processor configured to adjust a color tone of each voxel of the three-dimensional image according to a distance from a reference point, a reference line, or a reference plane in a three-dimensional space to each point of the three-dimensional data,
   wherein the processor is configured to:
      display, on the display, a graph indicating a relationship between the distance from the reference point, the reference line, or the reference plane to each point of the three-dimensional data and the color tone of each voxel of the three-dimensional image, and accept a user operation to change a slope of the graph; and
      change, for each point of the three-dimensional data, a color tone of a corresponding voxel of the three-dimensional image so that the slope of the graph has a magnitude corresponding to the accepted user operation.

\* \* \* \* \*